United States Patent
Yong et al.

(10) Patent No.: US 7,172,559 B2
(45) Date of Patent: Feb. 6, 2007

(54) DUAL-CHAMBER LIQUID RECEIVING AND CONTAINING DEVICE

(76) Inventors: Peter A. K. Yong, 3426 Onyx St., Torrance, CA (US) 90503; Mark J. Rispler, 201 Ocean Dr., Manhattan Beach, CA (US) 90266

(*) Notice: Subject to any disclaimer, the term of this patent is extended or adjusted under 35 U.S.C. 154(b) by 302 days.

(21) Appl. No.: 10/846,443

(22) Filed: May 14, 2004

(65) Prior Publication Data

US 2005/0004493 A1    Jan. 6, 2005

Related U.S. Application Data

(63) Continuation-in-part of application No. 10/834,405, filed on Apr. 29, 2004.

(60) Provisional application No. 60/494,773, filed on Aug. 13, 2003, provisional application No. 60/483,782, filed on Jun. 28, 2003.

(51) Int. Cl.
 *A61B 5/00* (2006.01)
 *B65D 81/00* (2006.01)
 *A61M 1/00* (2006.01)

(52) U.S. Cl. .................... 600/573; 604/324

(58) Field of Classification Search ............ 600/573, 600/575, 576, 579, 580; 604/321, 322, 323, 604/326, 346

See application file for complete search history.

(56) References Cited

U.S. PATENT DOCUMENTS

| | | | | |
|---|---|---|---|---|
| 3,982,898 A | * | 9/1976 | McDonald | 422/58 |
| 4,494,581 A | * | 1/1985 | Gordon | 141/1 |
| 4,559,049 A | * | 12/1985 | Haan | 604/350 |
| 4,573,983 A | * | 3/1986 | Annis | 604/322 |
| 4,769,215 A | * | 9/1988 | Ehrenkranz | 422/58 |
| 5,105,824 A | * | 4/1992 | Rasch | 600/575 |
| 5,711,310 A | * | 1/1998 | Vinayagamoorthy et al. | 600/580 |

* cited by examiner

*Primary Examiner*—Max F. Hindenburg
*Assistant Examiner*—Jeffrey G. Hoekstra
(74) *Attorney, Agent, or Firm*—Walter A. Hackler

(57) ABSTRACT

A dual-chamber device for receiving and containing a liquid, particularly urine, employs a generally cylindrical body having a detachable top cover and an internal, transverse, funnel-shaped wall. The transverse wall has a central circular orifice and divides the body into lower and upper chambers for respectively receiving and retaining fore-stream and mid-stream urine liquid samples. A floatable orifice stopper in the lower chamber is responsive to fore-stream liquid filling the lower chamber to a predetermined level for closing the orifice, so that subsequent, mid-stream urine liquid is received into the upper chamber. A bottom cover has an upstanding stopper pushing column and a flexible, spring-like, annular web around a bottom cover pedestal region.

8 Claims, 3 Drawing Sheets

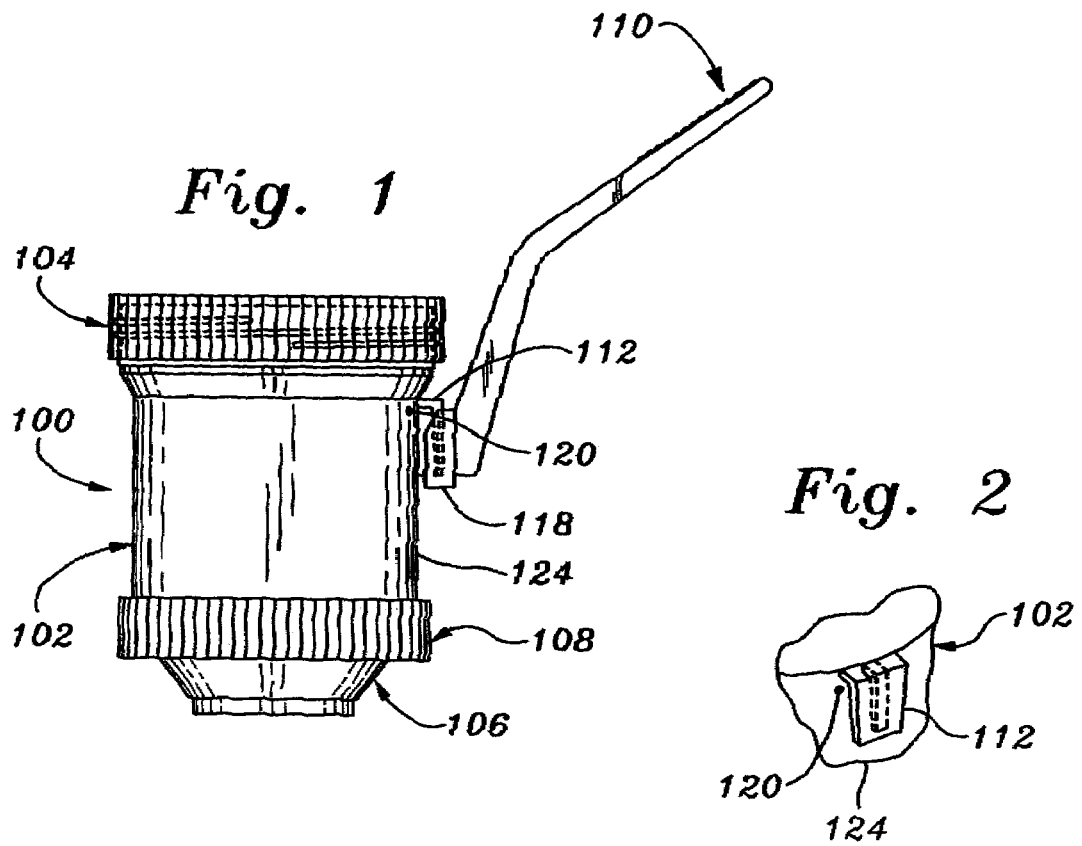
Fig. 1
Fig. 2
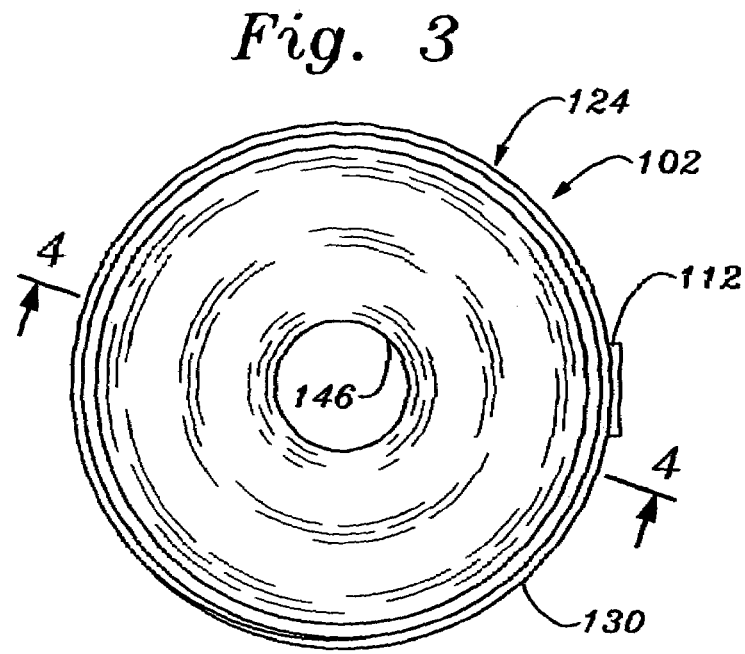
Fig. 3

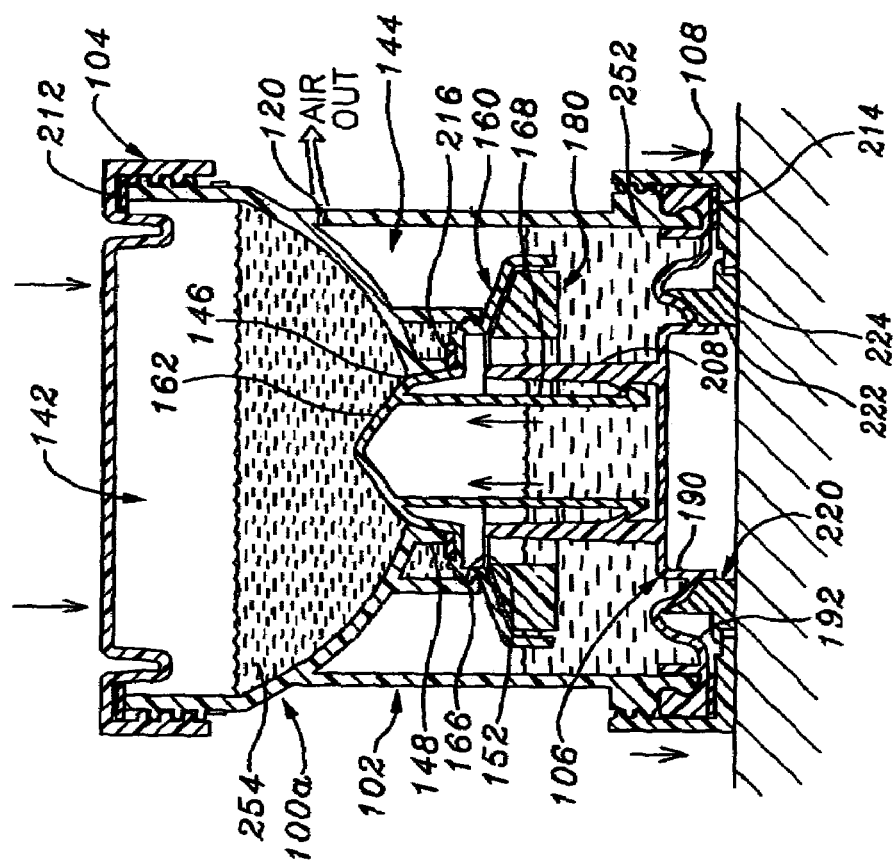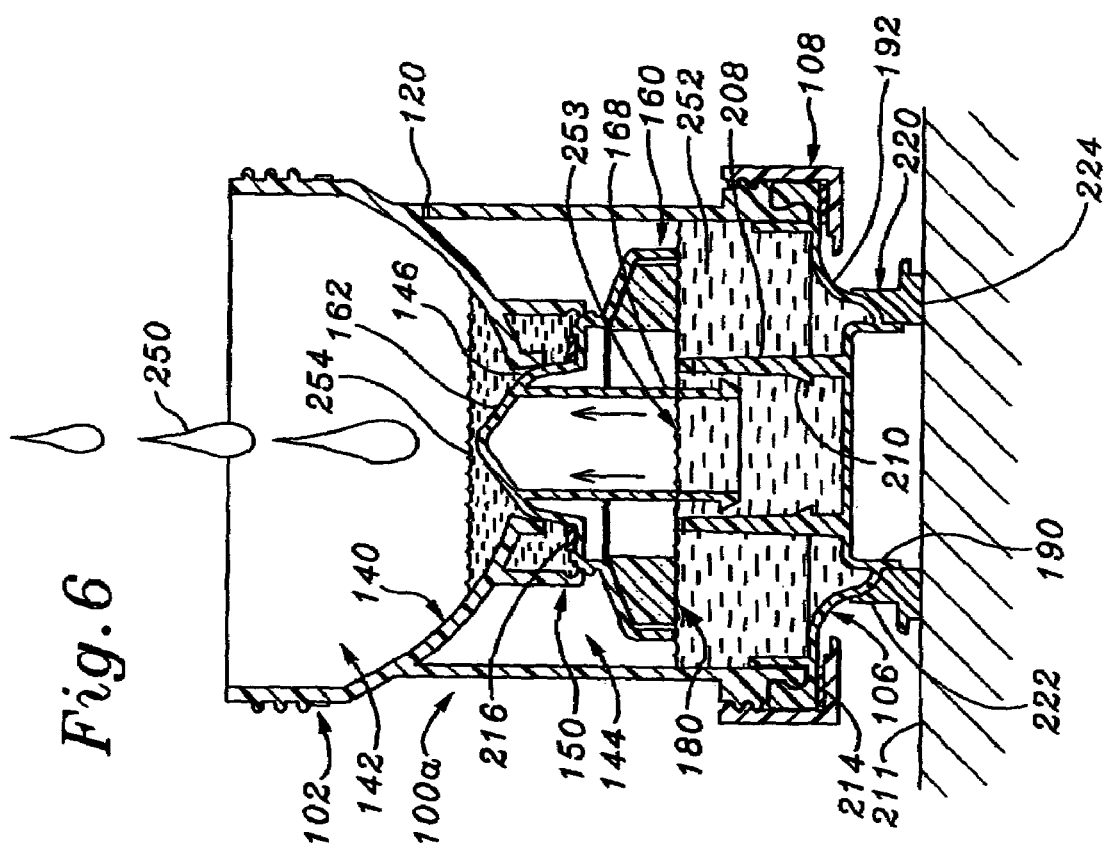

DUAL-CHAMBER LIQUID RECEIVING AND CONTAINING DEVICE

This application is a continuation in part (CIP) of application Ser. No. 10/834,405, filed Apr. 29, 2004, which is in turn a utility application converted from provisional application Ser. Nos. 60/483,782 and 60/494,773, filed respectively on Jun. 28, 2003 and Aug. 13, 2003. Application Ser. No. 10/834,405 (parent application) is incorporated herein in its entirety by specific reference.

FIELD OF THE INVENTION

The present invention relates to the general field of devices for collecting and separately containing dual samples of a liquid, more particularly to the collection and separately containing of dual samples of body fluids, and still more particularly to the collection and separate containing of dual samples of urine for analysis.

BACKGROUND DISCUSSION

In our above-cited parent application, there is disclosed a dual chamber device for collecting and retaining two sequential samples of liquid, in particular fore-stream and mid-stream samples of urine from an individual. The dual chamber device is disclosed as having a generally cylindrical body with a funnel-shaped transverse inner wall that divides the body into upper and lower liquid receiving and containing chambers of approximately the same volume. A circular orifice in the transverse inner wall provides liquid communication between the two chambers. A stopper disposed in the lower chamber below the orifice is responsive to liquid filling the lower chamber to a predetermined level to float upwardly to close the orifice, whereby liquid introduced into the device stops entering the lower chamber and starts filling the upper chamber.

There is disclosed in a preferred embodiment of the dual chamber device a snap-on bottom cover that is formed having a central pedestal region beneath the orifice stopper and having a column in engagement with the stopper. The central pedestal is surrounded by a thin flexible spring-acting annular web. After liquid has been collected in both the lower and upper chambers, the device body is capped and the device is pushed downwardly onto the bottom cover pedestal that is resting on a firm surface. This downward pushing action on the bottom cover pedestal causes the bottom cover flexible web to flex upwardly so that the bottom cover column engaging the stopper pushes the orifice stopper upwardly into tight engagement with the orifice. The over-center locking of the flexed web locks the orifice stopper tightly into the orifice to prevent liquid leakage between the lower and upper chambers. A flexible gasket or seal mounted on the orifice stopper provides orifice sealing integrity.

In a variation dual chamber device a bottom cover pedestal extension is disclosed for enabling greater upward flexing of the bottom cover web to further assure proper over-center locking of the web and positively assure tight locking of the orifice stopper into the orifice, regardless of device orientation and/or any careless handling of the liquid containing device.

The present inventors have, however, just discovered that the above-described downward pushing of the dual chamber device onto the bottom cover pedestal and/or bottom cover pedestal extension to cause upward flexing of the bottom cover web and pushing of the orifice stopper tightly into the orifice causes a substantial air pressure increase in the lower chamber above the liquid level therein. This increased air pressure in the lower chamber could possibly be sufficient to cause liquid in the lower chamber to bleed past the stopper in spite of its being tightly locked into the orifice. Assuming possibly unclean fore-stream urine is contained in the lower chamber and clean mid-stream urine, which is desired for bacterial analysis, is contained in the upper chamber, any such bleeding of the fore-stream urine from the lower chamber past the orifice stopper could contaminate the mid-stream urine contained in the upper chamber, rendering its bacteriological analysis results inaccurate.

It is, therefore, a principal objective of the present invention to provide for the venting of air pressure from the lower chamber so as to guarantee that pressure-caused bleeding of liquid from the lower chamber into the upper chamber will not occur.

SUMMARY OF THE INVENTION

A dual-chamber liquid receiving and retaining device comprises a liquid receiving and retaining body having an open top and an open bottom. A generally funnel-shaped transverse inner wall divides the body into an upper liquid receiving and retaining chamber and a lower liquid receiving and retaining chamber, the transverse inner wall having a central orifice which enables liquid flow communication between the upper and lower chambers. An orifice stopper disposed in the lower chamber beneath the orifice is responsive to liquid filling the lower chamber to a predetermined level for causing the stopper to float upwardly into sealing engagement with the orifice for stopping liquid flow into the lower chamber.

Included are a detachable body top cover and a detachable body bottom cover having an annular, spring-like, flexible web formed around a downwardly extending bottom cover region, the web being responsive to a downward pushing on the device onto the downwardly extending bottom cover region for deflecting upwardly in a manner causing a central upstanding region of the bottom cover to engage the stopper and force the stopper upwardly into the orifice. Means are provided for relieving air pressure in the lower chamber when the device is downwardly pushed onto the downwardly extending bottom cover region and the flexible web is deflected upwardly, thereby causing a lower chamber volume to be reduced.

There may be included a bottom cover extension sized for attachment to the downwardly extending bottom cover region and sized to provide a larger device body footprint and an additional height to the downwardly extending bottom cover region so as to assure the over-center locking of the web and secure locking of the stopper into the orifice.

The pressure relieving means includes a pinhole formed through a side wall of the device body into the lower chamber above the predetermined liquid level, the pinhole preferably having a diameter between about 0.01 mm and about 0.1 mm.

The dual chamber device may further a bottom cover locking ring sized to fit over the bottom cover and configured for threadable attachment to the body for locking the bottom cover tightly to the body.

BRIEF DESCRIPTION OF THE DRAWINGS

The present invention can be more readily understood by a consideration of the following detailed description when taken in conjunction with the accompanying drawings, in which:

FIG. 1 is an exterior, elevational view of the dual liquid receiving and containing device in accordance with the present invention, showing a device body having a removable top cover, a bottom cover with a detachable locking ring, and an ergonomic handle detachably attached to the device body, the body shown having a small pressure relief hole adjacent the handle-body attachment region (this FIG. corresponding to parent application FIG. 1);

FIG. 2 is a detail perspective drawing of a attachment element formed on the collection device body for receiving the T-slot element of the handle of FIG. 1 to thereby enable detachable attachment of the handle to the device, the pressure relief hole being shown adjacent the device body attachment element (this FIG. corresponding to parent application FIG. 4);

FIG. 3 is a top view of the device body with the top cover removed, showing a transverse wall that divides the body into two chambers, the transverse wall shown having a circular inlet orifice between the two chambers (this FIG. corresponding to parent application FIG. 5);

FIG. 6 is a vertical cross sectional drawing of the dual chamber device of FIG. 5 showing a flow of liquid being discharged into the upper chamber of the device, with the lower chamber having first been filled to a level causing an annular float to push an orifice stopper upwardly until an upper orifice sealing region of the stopper engages the orifice between the upper and lower chambers so as to stop the flow of liquid into the lower chamber and prevent liquid leakage between the two chambers, the pressure relief hole being shown in the device body wall (this FIG. corresponding to parent application FIG. 23); and FIG. 7 is a vertical cross sectional drawing similar to FIG. 6, but showing the upper chamber filled with liquid and the top cover attached to the device body, and showing the device pushed downwardly onto a flat surface sufficiently to flex the bottom cover web in a over-center locking condition pushing the bottom cover base upwardly into the lower chamber and thereby pushing the stopper orifice sealing region into positively locked engagement with the orifice and the orifice locking flange, thereby assuring no liquid leakage can occur between the two chambers, and showing air being vented from the lower chamber through the pressure relief hole in the device body wall (this FIG. corresponding to parent application FIG. 24).

In the various FIGS. the same elements and features are given the same reference number. In general the reference numbers used in the parent application will be used in this CIP application to avoid confusion.

DESCRIPTION OF THE PREFERRED EMBODIMENT

Figure 4:
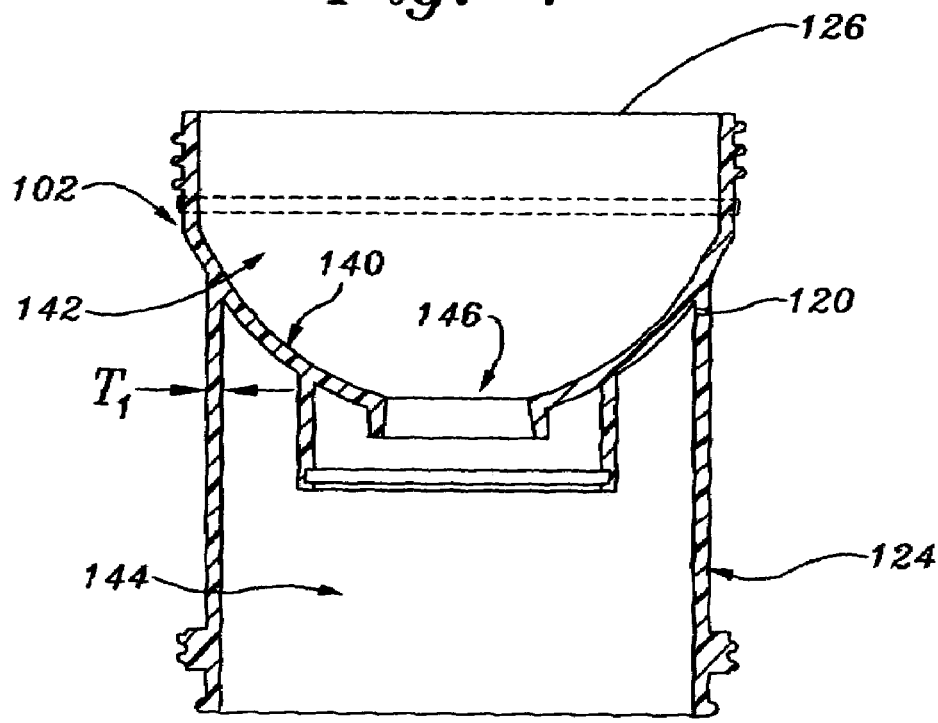
FIG. 4 is a vertical cross sectional view looking along line 4—4 of FIG. 3, showing the transverse inner wall that is generally funnel shaped and which divides the device body into upper and lower liquid receiving and retaining chambers, and showing an annular, undercut locking flange located around the transverse inner wall orifice, and showing the pressure relief hole formed through a device body wall in an upper region of the lower chamber (this FIG. corresponding to parent application FIG. 6)

There is shown in FIG. 1 a dual-chamber, liquid receiving and containing device 100 (hereinafter, for the sake of brevity, usually referred to as the "dual-chamber device") which may advantageously be used to receive a flow of urine from a patient and contain the urine flow as separate fore-stream and mid-stream flow portions, as described below.

Shown comprising dual-chamber device 100 are a generally cylindrical device body or liquid cup 102, a top cover or cap 104 that is detachably attached at an open upper end of the body, a bottom cover or cap 106 that is attached to an open bottom of the body, a bottom cover locking ring 108 that is threaded onto the body to secure the bottom cover to the body and an angled handle 110 that is detachably attached to the body by a tapered fitting 112 projecting from upper regions of the device body. Shown adjacent fitting 112 is a microscopic pressure relief hole 120 that extends through a device body outer wall 124 at the highest point of lower chamber 144 so as to be as high as possible above liquid collected in the lower chamber. Hole 120 (which is shown greatly exaggerated in size in all relevant FIGS. for purposes of clarity) may be between about 0.01 mm and about 0.05 mm in diameter.

FIG. 3 shows a top view of device body 102, which may be constructed of a rigid plastic material, such as high density polypropylene, and may be either transparent, translucent or opaque.

As shown in the vertical cross section of FIG. 4 device body wall 124 may have a thickness, $T_1$, that is about 0.05 inches. Formed internally across device outer wall 124 is a funnel-shaped transverse inner wall 140 that divides device body 102 into respective upper and lower chambers 142 and 144 having respective volumes for urine collection of about 80 ml and about 100 ml. A central, circular orifice 146 is formed in transverse inner wall.

Device body 102 is otherwise configured as described in our parent application.

Figure 5:
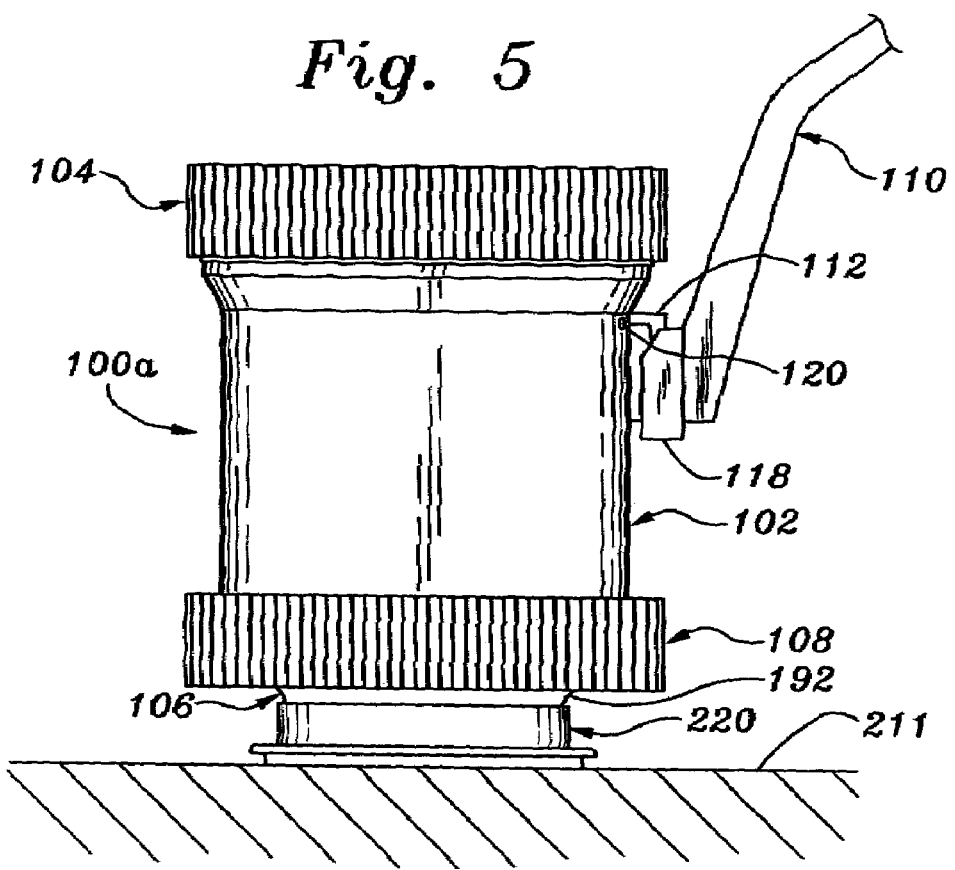
FIG. 5 (which corresponds to parent application FIG. 20) depicts a variation dual chamber device 100a that is identical to dual chamber device 100 depicted in FIG. 1 except for a bottom extension 220 that is installed onto bottom cover 106 to provide a slightly greater height to assure over-center locking of bottom cover flexible web 192, as well as to provide a greater device "foot print" for stability.

FIG. 5 (which corresponds to parent application FIG. 20) depicts a variation dual chamber device 100a that is identical to dual chamber device 100 depicted in FIG. 1 except for a bottom extension 220 that is installed onto bottom cover 106 to provide a slightly greater height to assure over-center locking of bottom cover flexible web 192, as well as to provide a greater device "foot print" for stability.

In the vertical cross sectional drawing of FIG. 6, (which corresponds to parent application FIG. 23) represents a liquid 250, such as a patient's urine, is shown being discharged into upper chamber 142 of device body 102, lower chamber 144 being shown already filled with the liquid (urine) which has caused a float 180 to push an orifice stopper 160 upwardly so that a stopper region 162 is pushed into sealing relationship with orifice 146, whereupon the liquid has then started filling upper chamber 142. Assuming that device 100a is used for the collection of a patient's urine for bacteriological analysis, urine 252 contained in lower chamber 144 should constitute fore-stream urine, the lower chamber having sufficient volume to assure that urine 254 being collected in upper chamber 142 will constitute uncontaminated mid-stream urine. An upper surface 253 of urine 252 coincides with the predetermined urine level in lower chamber 144 to which orifice stopper 160 is responsive for being floated upwardly into sealing engagement with orifice 146.

A vertical support column 168 depending from an orifice stopper skirt region 164 is telescopically received into a larger diameter guide column 208 extending upwardly from bottom cover 106. The upward movement of orifice stopper 160 is thus perfectly guided and restricted within bottom cover guide column 20. At this point, bottom cover annular flexible web 192 remains in its device pre-use, unflexed condition.

FIG. 6 is configured as disclosed in our parent application.

In the vertical cross sectional drawing of FIG. 7, which is similar to FIG. 6 (and corresponds to FIG. 24 of our parent application), dual-chamber device 100*a* is shown in its post-use condition with top cover 104 attached to device body 102. Device 100*a* is also shown pressed downwardly onto firm surface 211 so that bottom cover flexible web 192 flexes to an extent that a base region or bottom cover pedestal 190 and bottom cover extension 220 are fully recessed into device body 102. This causes bottom cover column 210 to push orifice stopper 160 upwardly into tight sealing relationship with orifice 146 with a stopper seal 216 forced in a sealing relationship against lower regions of an orifice ring 148.

The over-center locking of bottom cover web 192 locks bottom cover pedestal 190 in its upward position shown, thereby securely locking orifice stopper 160 into orifice 146 (as described above) so that regardless of any rough handling of device 100*a*, no liquid 252 can leak from lower chamber 144 into liquid 254 held in upper chamber 142.

Assuming lower chamber liquid 252 is fore-stream urine and upper chamber liquid 254 is mid-stream urine, the upper chamber mid-stream urine would be used for bacteriological analysis, and device 100*a* still containing lower chamber fore-stream urine would then be discarded.

It will, however, be appreciated that when device 100*a*, or device 100 without bottom cove extension 220) is pushed downwardly to flex bottom cover web 192 and cause bottom cover central region pedestal 190 and bottom cover extension (for device 100*a*) to be pushed upwardly into lower chamber 144, the lower chamber volume is decreased, causing a high air pressure in the lower chamber region above liquid 252, This high air pressure may be sufficient to cause bleeding of liquid 252 from lower chamber 144 past orifice stopper 160 into upper chamber 142 and possible contamination of upper chamber liquid 254. Device body hole 120 is provided for venting air from lower chamber 144 to relieve pressure therein and thereby prevent any liquid 252 from bleeding past orifice stopper 160.

FIG. 7 is otherwise configured as described for FIG. 23 in our parent application.

Thus, there has been described above a dual-chamber device for collecting and storing liquid samples (specifically urine samples) with lower chamber pressure relief for purposes of illustrating the manner in which the present invention may be used to advantage. It will, however, be appreciated that the invention is not limited thereto but includes any and all variations and modifications which may occur to those skilled in the art without violating the scope and spirit of the claims as appended hereto.

What is claimed is:

1. A dual-chamber liquid receiving and retaining device which comprises:
   a. a liquid receiving and retaining body, said body having an open top and an open bottom;
   b. a generally funnel-shaped transverse inner wall dividing said body into an upper liquid receiving and retaining chamber and a lower liquid receiving and retaining chamber, said transverse inner wall having a central orifice which enables liquid flow communication between said upper and lower chambers;
   c. an orifice stopper disposed in said lower chamber beneath said orifice, said stopper being responsive to liquid filling said lower chamber to a predetermined liquid level for causing the stopper to float upwardly into sealing engagement with said orifice for stopping liquid flow into the lower chamber;
   d. a detachable body top cover;
   e. a detachable body bottom cover having an annular, spring-like, flexible web formed around a downwardly extending bottom cover region, said web being responsive to a downward pushing on the device onto said downwardly extending bottom cover region for deflecting upwardly in a manner causing a central upstanding region of the bottom cover to engage said stopper and force the stopper upwardly into said orifice; and
   f. means, disposed in said lower chamber, for relieving air pressure in said lower chamber when the device is downwardly pushed onto said downwardly extending bottom cover region and said flexible web is deflected upwardly, thereby causing a lower chamber volume to be reduced.

2. The dual-chamber device as claimed in claim 1, including a bottom cover extension sized for attachment to said downwardly extending bottom cover region, said bottom cover extension being sized to provide a larger device body footprint and an additional height to the downwardly extending bottom cover region so as to assure said over-center locking of the web and secure locking of the stopper into the orifice.

3. The dual-chamber device as claimed in claim 1, wherein said pressure relieving means includes a microscopic pinhole formed through a side wall of said device body into said lower chamber above the predetermined liquid level.

4. The dual-chamber device as claimed in claim 3, wherein said pinhole has a diameter between 0.01 mm and 0.05 mm.

5. The dual-chamber device as claimed in claim 1, including a bottom cover locking ring sized to fit over said bottom cover and configured for threadable attachment to the body for locking the bottom cover tightly to the body.

6. A dual-chamber liquid receiving and retaining device which comprises:
   a. a liquid receiving and retaining body, said body having an open top and an open bottom;
   b. a generally funnel-shaped transverse inner wall dividing said body into an upper liquid receiving and retaining chamber and a lower liquid receiving and retaining chamber, said transverse inner wall having a central orifice which enables liquid flow communication between said upper and lower chambers;
   c. an orifice stopper disposed in said lower chamber beneath said orifice, said stopper being responsive to liquid filling said lower chamber to a predetermined liquid level for causing the stopper to float upwardly into sealing engagement with said orifice for stopping liquid flow into the lower chamber;
   d. a detachable body top cover;
   e. a detachable body bottom cover having an annular, spring-like, flexible web formed around a downwardly extending bottom cover region, said web being responsive to a downward pushing on the device onto said downwardly extending bottom cover region for deflecting upwardly in a manner causing a central upstanding region of the bottom cover to engage said stopper and force the stopper upwardly into said orifice; and f. a pinhole formed through a side wall of said device body into said lower chamber above the predetermined liquid level to relieve pressure in the lower chamber when the device is downwardly pushed onto said downwardly extending bottom cover region and said flexible web is deflected upwardly, thereby causing a lower chamber volume to be reduced, said pinhole having a diameter between 0.01 mm and 0.05 mm.

7. The dual-chamber device as claimed in claim 6, including a bottom cover extension sized for attachment to said downwardly extending bottom cover region, said bottom cover extension being sized to provide a larger device body footprint and an additional height to the downwardly extending bottom cover region so as to assure said over-center locking of the web and secure locking of the stopper into the orifice.

8. The dual-chamber device as claimed in claim 6, including a bottom cover locking ring sized to fit over said bottom cover and configured for threadable attachment to the body for locking the bottom cover tightly to the body.

* * * * *